US008865921B2

(12) United States Patent
Muñoz De Diego et al.

(10) Patent No.: US 8,865,921 B2
(45) Date of Patent: Oct. 21, 2014

(54) METHOD FOR THE PREPARATION OF 2,5-FURANDICARBOXYLIC ACID AND FOR THE PREPARATION OF THE DIALKYL ESTER OF 2,5-FURANDICARBOXYLIC ACID

(75) Inventors: Cesar Muñoz De Diego, Amsterdam (NL); Matheus Adrianus Dam, Amsterdam (NL); Gerardus Johannes Maria Gruter, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 185 days.

(21) Appl. No.: 13/497,690

(22) PCT Filed: Oct. 6, 2010

(86) PCT No.: PCT/NL2010/050654
§ 371 (c)(1),
(2), (4) Date: Jul. 9, 2012

(87) PCT Pub. No.: WO2011/043661
PCT Pub. Date: Apr. 14, 2011

(65) Prior Publication Data
US 2012/0271060 A1    Oct. 25, 2012

Related U.S. Application Data

(60) Provisional application No. 61/249,395, filed on Oct. 7, 2009.

(30) Foreign Application Priority Data

Oct. 7, 2009    (NL) ..................................... 2003606

(51) Int. Cl.
*C07D 307/68*    (2006.01)

(52) U.S. Cl.
CPC ................................. *C07D 307/68* (2013.01)
USPC ....................................................... 549/485

(58) Field of Classification Search
CPC .................................................... C07D 307/68
USPC ....................................................... 549/485
See application file for complete search history.

(56) References Cited

U.S. PATENT DOCUMENTS

| 2,628,249 | A | 2/1953 | Bruno |
| 2,673,860 | A | 3/1954 | Kuhn et al. |
| 4,977,283 | A | 12/1990 | Leupold et al. |
| 2009/0156841 | A1 | 6/2009 | Sanborn et al. |

FOREIGN PATENT DOCUMENTS

| EP | 0356703 A2 | 3/1990 |
| GB | 621971 | 10/1947 |
| JP | 2009001519 | 6/2007 |
| JP | 2009242312 | 10/2009 |
| RU | 636233 | 6/1976 |
| WO | 01/72732 A2 | 10/2001 |
| WO | 2006/063220 A2 | 6/2006 |
| WO | 2007/104515 A1 | 9/2007 |
| WO | 2008/054804 A2 | 5/2008 |
| WO | 2009/030512 A2 | 3/2009 |
| WO | 2009/076627 A2 | 6/2009 |
| WO | WO 2009/076627 A2 | 6/2009 |
| WO | 2010/132740 A2 | 11/2010 |

OTHER PUBLICATIONS

Boisen et al., "Process integration for the conversion of glucose to 2,5-furandicarboxylic acid", Chemical Engineering Research and Design, Part A, Institution of Chemical Engineers, vol. 87, No. 9, pp. 1318-1327, 2009.
Grabowski et al., "The Electrochemical Oxidation of 5-Hydroxymethyfurfural With the Nickel Oxide/Hydroxide Electrode", Electrochimica ACTA, vol. 36, No. 13, p. 1995, 1991.
Haworth et al., "The Conversion of Sucrose into Furan Compounds. Part II. Some 2: 5-disubstituted tetrahydrofurans and their products of ring scission", Journal of the Chemical Society, pp. 1-4, 1945.
Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts", Adv. Synth. Catal., vol. 343, No. 1, pp. 102-111, 2001.
Tong et al., "Biomass into chemicals: Conversion of sugars to furan derivatives by catalytic processes", Applied Catalysis A: General, vol. 385, No. 1-2, pp. 1-13, 2010.
English translation of a Chinese Office Action dated Dec. 4, 2013 for a counterpart foreign application.
English translation of communication dated Dec. 4, 2013 from a counterpart foreign (Chinese) application.

*Primary Examiner* — Taofiq A Solola
(74) *Attorney, Agent, or Firm* — John S. Sopko; Hoffman & Baron, LLP

(57) ABSTRACT

A method for the preparation of 2,5-furan dicarboxylic acid includes the step of contacting a feed comprising a compound selected from the group consisting of 5-hydroxymethylfurfural ("HMF"), an ester of 5-hydroxymethyl-furfural, 5-methylfurfural, 5-(chloromethyl)furfural, 5-methylfuroic acid, 5-(chloromethyl)furoic acid, 2,5-dimethylfuran and a mixture of two or more of these compounds with an oxidant in the presence of an oxidation catalyst at a temperature higher than 140° C.

10 Claims, No Drawings

METHOD FOR THE PREPARATION OF 2,5-FURANDICARBOXYLIC ACID AND FOR THE PREPARATION OF THE DIALKYL ESTER OF 2,5-FURANDICARBOXYLIC ACID

CROSS-REFERENCE TO RELATED APPLICATIONS

This application is the National Stage of International Application No. PCT/NL2010/050654, filed Oct. 6, 2010, which claims the benefit of Netherlands Application No. 2003606, filed Oct. 7, 2009, and U.S. Provisional Application No. 61/249,395, filed Oct. 7, 2009, the contents of all of which are incorporated by reference herein.

FIELD OF THE INVENTION

The present invention relates to a method for the preparation of 2,5-furandicarboxylic acid ("FDCA") from 5-hydroxymethylfurfural ("HMF") and/or derivatives thereof. FDCA can be produced in particular from esters of HMF, such as for example 5-acetoxymethylfurfural (AMF) or a mixture of one or more of these compounds with HMF, such as for example from a mixture of AMF and HMF. The invention further relates to a process for the preparation of the dialkyl ester of 2,5-furandicarboxylic acid.

BACKGROUND OF THE INVENTION 2,5-Furandicarboxylic acid, also known as dehydromucic acid is a furan derivative. This organic compound was first obtained by Fittig and Heinzelmann in 1876. The first review, by Henry Hill was published in 1901 (Am. Chem. Journ. 25, 439). FDCA was more than 125 years later identified by the US Department of Energy as one of 12 priority chemicals for establishing the "green" chemistry industry of the future. However, to date, no commercial process exists for its production. On laboratory scale it is often synthesized from 5-hydroxymethylfurfural (HMF), which in turn can be obtained from carbohydrate containing sources such as glucose, fructose, sucrose and starch. From fructose and glucose HMF is obtained by acidic elimination of three moles of water.

The derivatives of HMF are identified as potential and versatile fuel components and precursors for the production of plastics. The polyester from FDCA dimethyl diester and ethylene glycol was first reported in 1946 (GB 621,971).

WO 01/72732 describes the oxidation of HMF to FDCA. The maximum FDCA yield reported is 59%, obtained at 105° C. The oxidation of HMF in an aqueous medium with oxygen using a catalyst from the Pt-group is described in U.S. Pat. No. 4,977,283. Taarning et al. described the oxidation of HMF over gold based catalysts (ChemSusChem, 2008, 1, 1-4).

Partenheimer et al (Adv. Synth. Catal. 2001, 343, pp 102-11) describe the synthesis of 2,5-furandicarboxylic acid by catalytic air-oxidation of 5-hydroxymethylfurfural with metal/bromide catalysts such as Co/Mn/Br in acetic acid at temperatures ranging from 50 to 125° C. With the Co/Mn/Br catalyst the highest FDCA yield obtained is 35.2% (Table 3, experiment 4). On page 103 of the same paper, under the header "products formed" it is stated: "A side reaction is the esterification of the alcohols to form the more oxidatively stable acetate . . . " As apparently 5-hydroxymethylfurfural reacts with acetic acid a loss of the starting material takes place. Further, in the reaction scheme given in FIG. 1 on page 103, it is indicated that 5-(acetoxymethyl)furfural is an end-point. There is no further reaction of this compound indicated to FDCA (in contrast to the ester of the intermediate product 5-(acetoxymethyl)furan-2-carboxylic acid). In other words, the 5-(acetoxymethyl)furfural (AMF) formed through reaction of HMF with acetic acid solvent, is not oxidized to FDCA and its formation leads therefore to yield loss.

This result was confirmed in U.S. 2009/0156841. Although the intention of the process according to U.S. 2009/0156841 was to obtain FDCA, the product isolated and erroneously characterized as being FDCA was in fact the starting material acetoxymethyl furfural (AMF). Under the low temperature conditions deployed (100° C.), AMF is quite stable, as was already reported by Partenheimer (see above).

In U.S. 2009/0156841 a $^1$H NMR spectrum is shown in FIG. 8 and suggested that it is the spectrum of the product that was identified as FDCA. However, this is not the case. The $^1$H NMR spectrum of the product shown in FIG. 8 is the same as that in FIG. 6 and represents the starting material AMF. The 1H NMR spectrum of FDCA shows a singlet at a shift of about 7.26 ppm. Moreover, the product is described as a tan solid. In the experience of the present inventors, AMF is a tan solid, while FDCA is a white solid. It would seem that no FDCA was obtained in the experiments according to U.S. 2009/0156841.

The experiments executed under the conditions of U.S. 2009/0156841 were repeated. These comparative experiments confirm the low reactivity of AMF under conditions given in U.S. 2009/0156841. Thus, a person skilled in the art would therefore have concluded that FDCA cannot be obtained in interesting yields from AMF using the conditions that are reported in U.S. 2009/0156841, i.e., using a Co/Mn/Br catalyst in acetic acid at between 85 and 110° C. within a time frame of from 100 and 150 minutes. In Example 7 of U.S. 2009/0156841, slightly more than 50% of the starting material was the only product isolated from the reaction.

SUMMARY OF THE INVENTION

The present inventors have now surprisingly found that when using an oxidation catalyst, e.g., based on both cobalt and manganese and containing a bromide, at temperatures higher than 140° C., derivatives of HMF, and in particular esters of HMF optionally in combination with HMF, such as for example 5-(acetoxymethyl)furfural (AMF) can be oxidized to FDCA in high yields.

DETAILED DESCRIPTION OF THE INVENTION

Thus, in a first aspect the invention provides a method for the preparation of 2,5-furan dicarboxylic acid comprising the step of contacting a feed comprising a compound selected from the group consisting of 5-hydroxymethylfurfural ("HMF"), an ester of 5-hydroxymethyl-furfural, 5-methylfurfural, 5-(chloromethyl)furfural, 5-methylfuroic acid, 5-(chloromethyl)furoic acid, 2,5-dimethylfuran and a mixture of two or more of these compounds with an oxidant in the presence of an oxidation catalyst at a temperature higher than 140° C. The feed may optionally comprise 5-hydroxymethylfurfural as a further compound.

The invention described hereinafter may use any of the compounds described above in the feed. A preferred ester of HMF contains an ester moiety of an alkyl carboxylic acid wherein the alkyl group contains up to 6 carbon atoms, preferably from 1 to 5 carbon atoms, i.e. methyl, ethyl, propyl, isopropyl, butyl, 2-butyl, tert-butyl, pentyl, 2-pentyl, neopentyl and 3-pentyl. Particularly preferred are alkyl groups with 1 to 4 carbon atoms. There is a preference for methyl, giving (5-acetoxymethyl)furfural. Hence, 5-acetoxymethylfurfural is the preferred feedstock, by itself or in combination with HMF.

In another aspect of the invention, we have also investigated the oxidation of other furan-based substrates under the process conditions according to the current invention. We have been able to convert 5-(chloromethyl)furfural, 5-(chloromethyl)furoic acid, 5-methylfurfural, 5-methylfuroic acid and 2,5-dimethylfuran all to FDCA in very interesting yields.

In WO 2007/104515 and WO 2009/030512, the synthesis of esters of HMF such as 5-acetoxymethylfurfural (AMF) from biomass sources is described. Given the higher stability of the HMF esters than HMF and hence improved production pathways and given the fact that upon oxidation in acetic acid the acetoxy functionality that was obtained from acetic acid is now liberated as acetic acid and given the green reputation of these esters, they were considered by the present inventors as interesting starting point in the preparation of furan-based monomers that could be used for the production of furandicarboxylic acid-based polyesters, for instance as an alternative for PET or FDCA-based polyamids (nylons). The most important conventional, oil-based, polyester monomer to produce PET is Purified Terephthalic acid (PTA) and its dialkyl ester DiMethyl Terephthalate (DMT).

AMF can be obtained from biomass sources as described in WO 2007/104515 and WO 2009/030512. Depending on the process conditions the product obtained in accordance with the process of these references may also contain HMF.

FDCA, the product of the reaction can be used in the preparation of a polyester, by reaction of FDCA or its dialkyl ester with a suitable diol. Such polyester preparations are preferably performed by transesterification, whereby the di-methyl ester or di-ethyl ester of FDCA is used and wherein the methyl or ethyl groups are exchanged in the form of a volatile alcohol during the transesterification with the diol.

The oxidation catalyst can be selected from a variety of oxidation catalysts, but is preferably a catalyst based on both cobalt and manganese and suitably containing a source of bromine, preferably a bromide.

The bromine source can be any compound that produces bromide ions in the reaction mixture. These compounds include hydrogen bromide, sodium bromide, elemental bromine, benzyl bromide and tetrabromoethane. Also other bromine salts, such as an alkali or alkaline earth metal bromide or another metal bromide such as $ZnBr_2$ can be used. There is a preference for hydrobromic acid or sodium bromide. The amount of bromine mentioned in here relates to the amount measured as Br relative to cobalt.

Suitable metal bromide catalysts employed in all of the processes of this invention comprise a cobalt compound and a manganese compound and a bromine-containing compound. Preferably these compounds are soluble in the reaction mixture.

Preferably, the catalyst comprises both Co and Mn. The metal and bromide catalyst contains, in addition to bromide, Co and Mn and optionally may contain one or more additional metals, in particular Zr and/or Ce. Alternative and suitable catalysts are described in W. Partenheimer, Catalysis Today 23 (2), 69-158 (1995) in particular on pages 89-99, included herein by reference.

Each of the metal components can be provided in any of their known ionic forms. Preferably the metal or metals are in a form that is soluble in the reaction solvent. Examples of suitable counterions for cobalt and manganese include, but are not limited to, carbonate, acetate, acetate tetrahydrate and halide, with bromide being the preferred halide.

As described in Partenheimer, ibid, pages 86-88, suitable solvents for use in the processes of the present invention, described above, preferably have at least one component that contains a monocarboxylic acid functional group. The solvent may also function as one of the reagents. The processes may be run in a solvent or solvent mixture that does not contain an acid group. In that case, preferably one of the reagents does contain a monocarboxylic acid functional group. Suitable solvents can also be aromatic acids such as benzoic acid and derivatives thereof. A preferred solvent is an aliphatic $C_2$-$C_6$ monocarboxylic acid, such as but not limited to acetic acid, propionic acid, n-butyric acid, isobutyric acid, n-valeric acid, trimethylacetic acid, and caproic acid and mixtures thereof. Said mixtures may also include benzene, acetonitrile, heptane, acetic anhydride, chlorobenzene, o-dichlorobenzene, and water. The most preferred solvent is acetic acid ("AcOH").

The oxidant in the processes of the present invention is preferably an oxygen-containing gas or gas mixture, such as, but not limited to air and oxygen-enriched air. Oxygen by itself is also a preferred oxidant.

The processes of the instant invention described above can be conducted in a batch, semi-continuous or continuous mode. Especially for the manufacture of FDCA, operation in the batch mode with increasing temperature at specific times, increasing pressure at specific times, variation of the catalyst concentration at the beginning of the reaction, and variation of the catalyst composition during the reaction is desirable. For example, variation of the catalyst composition during the reaction can be accomplished by addition of cobalt and/or manganese and/or zirconium, and/or cerium, and/or bromide at specified times.

The pressure in a commercial oxidation process may vary within wide ranges. When a diluent is present, and in particular with acetic acid as diluent, the temperature and the pressure in such a process are not independent. The pressure is determined by the solvent (e.g., acetic acid) pressure at a certain temperature. The pressure of the reaction mixture is preferably selected such that the solvent is mainly in the liquid phase. In practice this means that pressures between 5 and 100 bar can be used with a preference for pressures between 10 and 80 bar. In case the oxidant is an oxygen-containing gas, such as air, the gas can be continuously fed to and removed from the reactor, or the gas can be supplied all at the start of the reaction. In the latter case, the pressure of the system will depend on the headspace volume and the amount of gas required to convert the starting material. It is clear that in the latter case, the pressure of the system may be significantly higher than the pressure in a process wherein an oxygen containing gas is continuously fed and removed. In the case of continuously feeding and removing the oxidant gas to and from the reactor, the oxygen partial pressure will suitably be between 1 and 30 bar or more preferably between 1 and 10 bar.

The temperature of the reaction mixture is at least 140° C., preferably from 140 and 200° C., most preferably between 160 and 190° C. Temperatures higher than 180° C. may lead to decarboxylation and to other degradation products. Good results to FDCA have been achieved at a temperature of about 180° C.

Molar ratios of cobalt to manganese (Co/Mn) are typically 1/1000-100/1, preferably 1/100-10/1 and more preferably 1/10-4/1.

Molar ratios of bromine to metals (e.g. Br/(Co+Mn)) are typically 0.001-5.00, preferably 0.01-2.00 and more preferably 0.1-0.9.

Catalyst concentration (Co+Mn) is typically from 0.1 to 10 mol %, relative to the substrate, with a preference for concentrations from 2 to 6 mol %. Good results were obtained in general with catalyst concentrations of around 4 mol %.

The starting materials for the production of FDCA may originate from a carbohydrate source as described above. Examples of such disclosures are WO 2007/104515 and WO 2009/030512. Accordingly, the invention also provides a method for the preparation of 2,5-furandicarboxylic acid wherein a carbohydrate source is converted in the presence of an alkyl carboxylic acid into products comprising an HMF ester and optionally 5-hydroxymethyl furfural, from which is isolated a feed comprising the ester of HMF and optionally 5-hydroxymethyl furfural, and which method further comprises the subsequent step of contacting the feed with an oxidant in the presence of an oxidation catalyst, in particular a cobalt and manganese and bromide-containing catalyst, under appropriate reaction conditions, in particular at temperatures higher than 140° C.

In another aspect, the FDCA obtained according to the process of the present invention can be transformed using common esterification reactions to a diester by contacting the starting material under appropriate conditions with the relevant alcohol. Thus, in one aspect, the invention also relates to the use of FDCA obtained according to the process of the current invention in the preparation of a dialkylester of 2,5-dicarboxylic acid by reaction of the FDCA with a $C_1$-$C_5$ alkyl alcohol, preferably methanol to prepare the dimethyl ester of FDCA.

Accordingly, the present invention also provides a process for the preparation of a dialkyl ester of 2,5,-furan dicarboxylic acid, comprising the step of contacting a feed comprising a compound selected from the group consisting of 5-hydroxymethylfurfural ("HMF"), an ester of 5-hydroxymethyl-furfural, 5-methylfurfural, 5-(chloromethyl)furfural, 5-methylfuroic acid, 5-(chloromethyl)furoic acid, 2,5-dimethylfuran and a mixture of two or more of these compounds with an oxidant in the presence of an oxidation catalyst at a temperature higher than 140° C., and esterifying the thus obtained product. Preferably, the product is esterified with an alkyl alcohol, suitably having 1 to 5 carbon atoms.

The esterification of 2,5-furan dicarboxylic acid is known. As a specific example for the manufacture of these esters, reference is made to U.S. Pat. No. 2,673,860 wherein the diester is obtained by transesterification of another dicarboxylic acid ester in the presence of sulphuric acid. A more general description for the esterification of dicarboxylic acids is presented in U.S. Pat. No. 2,628,249. Accordingly, the invention provides a process for the preparation of a dialkyl ester of 2,5,-furan dicarboxylic acid, comprising the step of contacting a feed comprising a compound selected from the group consisting of 5-hydroxymethylfurfural ("HMF"), an ester of 5-hydroxymethyl-furfural, 5-methylfurfural, 5-(chloromethyl)furfural, 5-methylfuroic acid, 5-(chloromethyl)furoic acid, 2,5-dimethylfuran and a mixture of two or more of these compounds with an oxidant in the presence of an oxidation catalyst at a temperature higher than 140° C., and esterifying the thus obtained product.

In a further aspect of the invention, the di-methylester can be used in the preparation of polyester polymers by reaction with a diol. Reacting the di-methylester with a diol will result in the formation of methanol that quickly vaporises. In 1946 the polymerization of FDCA dimethyl ester with ethylene glycol was described as a first example of such a polymerization in GB 621,971.

Indeed, polyesters are generally made by a combined esterification/polycondenzation reaction between monomer units of a diol (e.g., ethylene glycol (EG)) and a dicarboxylic acid. Additives such as catalysts and stabilizers may be added to facilitate the process and stabilize the polyester towards degradation.

EXAMPLES

Experiments were carried out in parallel 8 ml magnetically stirred stainless steel batch reactors. The reactors are grouped in blocks containing 12 batch reactors. The standard procedure for all the reactions was as follows:

0.5 ml of starting material stock solution in acetic acid (0.78 mmol/ml) were added into a reactor lined with a Teflon insert. To the reactor 1 ml of a catalyst stock solution in acetic acid was subsequently added. In a typical experiment, a catalyst composition Co/Mn/Br with a relative 1-x-y ratio, the concentration of Co(OAc)$_2$* 4H$_2$O was varied. As a Mn source, Mn(OAc)$_2$*4H$_2$O was used and as a bromine source NaBr was used. The reactors were closed with a rubber septum, after which the reactors were sealed and pressurized to the desired air pressure, ranging from 20-60 bars. After pressurization, the block with 12 reactors was placed in the test unit which was preheated at the desired temperature, ranging from 100 to 220° C. After the desired reaction time, ranging from 0.5 hr to 24 hrs, the block is placed into an ice bath for 20 minutes. When the block had cooled down, it was depressurized. After opening, HPLC samples were prepared. First 5 ml of a saccharine solution in DMSO (11.04 mg/ml) was added to each reactor and the mixture was stirred for 5 minutes. Then 10 µl of this mixture was diluted to 1000 µl with water in a HPLC vial. The samples were analyzed using HPLC.

Example 1

Example 1 shows the selectivity of FDCA in the oxidation of HMF, of a HMF/AMF 3/2 mixture, of a HMF/AMF 2/3 mixture and of AMF, respectively, with 2.7 mol % Co catalyst (relative to substrate), and Co/Mn molar ratio of 1/1, so that the catalyst concentration (Co+Mn) amounted to 5.4 mol %. The Br/(Co+Mn) molar ratio was 1.0; 0.7; 0.4 and 0.1 at 0.26 M substrate concentration in acetic acid at 180° C. for 1 hr with 20 bar air. The amount of oxygen was 2.69 mol oxygen per mol substrate. Under these conditions, higher Br amounts give higher yields but when Br/(Co+Mn)>1, corrosion will be a problem on commercial scale. HMF gives slightly higher yields than AMF at one hour reaction time. The results of these experiments are given in Table 1.

Example 2

Example 2 shows the selectivity to FDCA for the AMF oxidation of Example 1, together with the comparative examples based on the experimental conditions described in U.S. 2009/0156841. In those comparative experiments (2a and 2b) 10 wt/wt % AMF in acetic acid was oxidized with 1.75 and 2.65 mol % Co catalyst and a fixed Br/(Co+Mn) molar ratio of 1.0 and a Co/Mn molar ratio of 1.0 at 100° C. and 30 bar for 2 hours. The amount of oxygen was 2.88 mol oxygen per mol substrate. Under these conditions, the yield of FDCA was lower than the result suggested in U.S. 2009/0156841 and also lower than the results obtained at higher temperature. The results of these experiments are given in Table 2.

Example 3

Example 3 shows the yield of FDCA in the oxidation of 5-methylfurfural (5MF) and 2,5-dimethylfurfural (DMF) at 180° C. with 2.7 mol % Co catalyst (relative to substrate), and Co/Mn ratio of 1/1, so that the catalyst concentration (Co+Mn) amounted to 5.4 mol %. The Br/(Co+Mn) molar ratio was 1.0, 0.7, 0.4 and 0.1. The substrate concentration was 0.26 M in acetic acid. The reaction temperature was at 180° C. and the reaction was conducted with 50 bars air. The amount of oxygen was 6.7 mol oxygen per mol substrate. Under these conditions, higher Br amounts give higher yields but when Br/(Co+Mn)>1, corrosion will be a problem on commercial scale. Reactions with 5-MF give higher yields than reactions with DMF. The results of these experiments are also given in Table 3.

TABLE 1

| Experiment No. | Substrate HMF/AMF molar ratio HMF | AMF | Br/(Co + Mn) | Substrate concentration [wt %] | Conversion [%] | s FDCA [%] |
|---|---|---|---|---|---|---|
| 1a | 1 | 0 | 1 | 3.3 | 100.00 | 76.66 |
| 1b | 3 | 2 | 1 | 3.8 | 100.00 | 71.19 |
| 1c | 2 | 3 | 1 | 4.0 | 100.00 | 77.66 |
| 1d | 0 | 1 | 1 | 4.4 | 100.00 | 64.82 |
| 1e | 1 | 0 | 0.7 | 3.3 | 100.00 | 78.08 |
| 1f | 3 | 2 | 0.7 | 3.8 | 100.00 | 66.96 |
| 1g | 2 | 3 | 0.7 | 4.0 | 100.00 | 75.14 |
| 1h | 0 | 1 | 0.7 | 4.4 | 100.00 | 60.64 |
| 1i | 1 | 0 | 0.4 | 3.3 | 100.00 | 73.27 |
| 1j | 3 | 2 | 0.4 | 3.8 | 100.00 | 65.67 |
| 1k | 2 | 3 | 0.4 | 4.0 | 100.00 | 73.21 |
| 1l | 0 | 1 | 0.4 | 4.4 | 100.00 | 57.36 |
| 1m | 1 | 0 | 0.1 | 3.3 | 100.00 | 67.92 |
| 1n | 3 | 2 | 0.1 | 3.8 | 100.00 | 60.92 |
| 1o | 2 | 3 | 0.1 | 4.0 | 100.00 | 69.64 |
| 1p | 0 | 1 | 0.1 | 4.4 | 100.00 | 46.85 |

TABLE 2

| Experiment No. | Temp [° C.] | Reaction time [Hours] | Catalyst concentration [(Co + Mn) mol %] | Mn/Co | Br/(Co + Mn) | $O_2$/Subs [mol/mol] | Substrate concentration [wt %] | Conversion [%] | s FDCA [%] |
|---|---|---|---|---|---|---|---|---|---|
| 1d | 180 | 1 | 5.4 | 1 | 1 | 2.69 | 4.4 | 100.00 | 64.82 |
| 1h | 180 | 1 | 5.4 | 1 | 0.7 | 2.69 | 4.4 | 100.00 | 60.64 |
| 1l | 180 | 1 | 5.4 | 1 | 0.4 | 2.69 | 4.4 | 100.00 | 57.36 |
| 1p | 180 | 1 | 5.4 | 1 | 0.1 | 2.69 | 4.4 | 100.00 | 46.85 |
| 2a | 100 | 2 | 3.5 | 1 | 1 | 2.88 | 10.0 | 100.00 | 23.48 |
| 2b | 100 | 2 | 5.3 | 1 | 1 | 2.88 | 10.0 | 100.00 | 29.05 |

TABLE 3

| Experiment No. | Substrate | Reaction time [Hours] | Br/(Co + Mn) | $O_2$/Subs [mol/mol] | Substrate concentration [wt %] | Conversion [%] | s FDCA [%] |
|---|---|---|---|---|---|---|---|
| 3a | 5-MF | 1 | 1 | 6.7 | 2.9 | 100.00 | 42.62 |
| 3b | 5-MF | 1 | 0.7 | 6.7 | 2.9 | 100.00 | 39.94 |
| 3c | DMF | 1 | 1 | 6.7 | 2.5 | 100.00 | 16.17 |
| 3d | DMF | 1 | 0.7 | 6.7 | 2.5 | 100.00 | 14.09 |
| 3e | DMF | 1 | 0.4 | 6.7 | 2.5 | 100.00 | 11.30 |
| 3f | DMF | 1 | 0.1 | 6.7 | 2.5 | 100.00 | 7.19 |

The invention claimed is:

1. A method for the preparation of 2,5-furan dicarboxylic acid comprising the step of contacting a feed comprising a compound selected from the group consisting of 5-hydroxymethylfurfural ("HMF"), an ester of 5-hydroxymethylfurfural, 5-methylfurfural, 5-(chloromethyl)furfural, 5-methylfuroic acid, 5-(chloromethyl)furoic acid, 2,5-dimethylfuran and a mixture of two or more of these compounds with an oxygen-containing gas, in the presence of an oxidation catalyst comprising both Co and Mn, and further a source of bromine, at a temperature between 140° C. and 200° C. at an oxygen partial pressure of 1 to 10 bar, wherein a solvent or solvent mixture comprising acetic acid or acetic acid and water mixtures is present.

2. The method according to claim 1, wherein the feed comprises a compound selected from the group consisting of 5-hydroxymethylfurfural ("HMF"), esters of HMF and a mixture thereof.

3. The method according to claim 1, wherein the oxidation catalyst comprises at least one additional metal.

4. The method according to claim 3, wherein the additional metal is Zr and/or Ce.

5. The method according to claim 1, wherein the temperature is between 160 and 190° C.

6. The method according to claim 1, wherein the feed comprises an ester of HMF having an ester moiety of an alkyl carboxylic acid wherein the alkyl group has up to 6 carbon atoms.

7. A process for the preparation of a dialkyl ester of 2,5,-furan dicarboxylic acid, comprising the step of contacting a feed comprising a compound selected from the group consisting of 5-hydroxymethylfurfural ("HMF"), an ester of 5-hydroxymethyl-furfural, 5-methylfurfural, 5-(chloromethyl)furfural, 5-methylfuroic acid, 5-(chloromethyl)furoic acid, 2,5-dimethylfuran and a mixture of two or more of these compounds with an oxygen-containing gas in the presence of an oxidation catalyst comprising both Co and Mn, and further a source of bromine, at a temperature between 140° C. and 200° C. at an oxygen partial pressure of 1 to 10 bar, wherein a solvent or solvent mixture comprising acetic acid or acetic acid and water mixtures is present, and esterifying the thus obtained product.

8. The process according to claim 7, wherein the product is esterified with a C1-C5 alkyl alcohol.

9. The process according to claim 8, wherein the C1-C5 alkyl alcohol is methanol and the dialkyl ester is the dimethylester of 2,5-furan dicarboxylic acid.

10. A method according to claim 2, wherein the feed comprises an HMF ester and optionally 5-hydroxymethyl furfural, which has been obtained by converting a carbohydrate source in the presence of an alkyl carboxylic acid.

\* \* \* \* \*